United States Patent
Ogura

(10) Patent No.: US 6,638,428 B2
(45) Date of Patent: Oct. 28, 2003

(54) METHOD OF PREVENTING FORMATION OF BUBBLES DURING FILTRATION OPERATIONS

(75) Inventor: Mieko Ogura, Newport Coast, CA (US)

(73) Assignees: Hitachi Chemical Research Center, Inc., Irvine, CA (US); Hitachi Chemical Co., LTD (JP)

(*) Notice: Subject to any disclaimer, the term of this patent is extended or adjusted under 35 U.S.C. 154(b) by 0 days.

(21) Appl. No.: 10/003,176

(22) Filed: Oct. 31, 2001

(65) Prior Publication Data

US 2002/0121480 A1 Sep. 5, 2002

Related U.S. Application Data

(60) Provisional application No. 60/244,672, filed on Oct. 31, 2000.

(51) Int. Cl.$^7$ .................... B01D 61/00; B01D 19/04; C02F 1/44
(52) U.S. Cl. .................... 210/650; 210/750; 210/218; 95/155; 422/44; 261/5
(58) Field of Search ................ 210/650, 644, 210/639, 634, 750, 799, 198.1, 218, 538, 539, 637; 261/DIG. 26, 215; 422/44, 45; 604/4.01, 6.15, 403; 95/149, 155, 157, 187, 206; 252/60, 62.3 R, 62.3 Q

(56) References Cited

U.S. PATENT DOCUMENTS

| | | | |
|---|---|---|---|
| 3,711,392 A | * | 1/1973 | Metzger ................. 210/603 |
| 4,159,933 A | | 7/1979 | Allington et al. |
| 4,211,115 A | * | 7/1980 | Engebreth ............... 73/863.86 |
| 4,664,844 A | * | 5/1987 | Bergold et al. ............ 30/100 |
| 4,846,976 A | * | 7/1989 | Ford ...................... 210/636 |
| 5,078,888 A | * | 1/1992 | Penticoff et al. ........... 210/639 |
| 5,130,037 A | * | 7/1992 | Swiatowski et al. ........ 252/61 |
| 5,340,449 A | | 8/1994 | Shukla |
| 5,843,734 A | * | 12/1998 | Shonaka et al. ........... 435/106 |
| 6,254,825 B1 | * | 7/2001 | Friedman ................ 422/44 |

FOREIGN PATENT DOCUMENTS

| | | |
|---|---|---|
| DE | 3715856 | 12/1988 |
| EP | 0776700 | 6/1997 |
| WO | WO 00/33050 | 6/2000 |

OTHER PUBLICATIONS

Marcel Dekker, Inc., Nico M. van Os, *Nonionic Surfactants, Organic Chemistry*, 1998, New York, New York.

* cited by examiner

Primary Examiner—W. L. Walker
Assistant Examiner—Krishnan S Menon
(74) Attorney, Agent, or Firm—Knobbe Martens Olson & Bear LLP.

(57) ABSTRACT

Formation of bubbles is prevented during filtration operation by placing an oil on top of a solution-to-be filtered, where the oil is not admixable with the solution and has a lower specific gravity than the solution. The oil seals the solution from air so that no bubbles are formed. The oil does not pass through the filter even after all collectable filtrate of the solution has passed therethrough.

18 Claims, No Drawings

METHOD OF PREVENTING FORMATION OF BUBBLES DURING FILTRATION OPERATIONS

CROSS-REFERENCE TO RELATED APPLICATIONS

This application claims priority to U.S. Provisional Application Ser. No. 60/244,672, filed on Oct. 31, 2000, the disclosure of which is herein incorporated by reference in its entirety.

BACKGROUND OF THE INVENTION

1. Field of the Invention

The present invention relates to a method of filtration of a solution using a membrane, and particularly to a method of preventing formation of bubbles during filtration operation.

2. Background Art

Suction operation processes are commonly employed techniques in the biological sciences. However, when surfactant- or detergent-containing solution is suctioned through membranes, the solution becomes infused with bubbles. This is quite problematic, since it reduces filtration efficiency, provides poor recovery, requires an additional labor of centrifugation to remove the bubbles, and creates potential contamination to the membrane and surrounding areas. Bubbles can be eliminated when suction power is reduced, however, a portion of solution still exists in the membrane, and it is difficult to recover all solution out of membrane. Although it is possible to recover all the solution by centrifugation without the occurrence of bubbles, this process is not desirable for automation.

High throughput automation is becoming more prevalent and desirable in research, and may often include a filtration step. However, centrifugation is not compatible with the automation process. One way of minimizing user intervention in high throughput automation processes is through utilization of vacuum filtration techniques. The drawback of using the vacuum filtration technique is the appearance of bubbles in the filtered solution.

Therefore, there is a need for an efficient and bubble-free methodology when utilizing a suction operation technique in the rapidly growing high throughput automation platform. Preventing the formation of bubbles during the vacuum filtration process increases sample recovery. In addition, vacuum pressure can be increased and vacuum time can be extended to increase sample recovery during the vacuum filtration process.

SUMMARY OF THE INVENTION

In view of the above, the present invention provides an embodiment wherein a method of filtration comprises: (i) loading a solution-to-be filtrated upstream of a membrane filter, said solution containing components forming bubbles during filtration operation; (ii) covering the solution with a layer of an oil to prevent formation of bubbles from the solution, said oil being non-admixable with the solution and having a lower specific gravity than the solution; (iii) filtrating the solution through the membrane filter wherein the oil stays on the membrane filter; and (iv) recovering a filtrate.

The solution contains detergents or other components, and thus an oil may be slightly admixable depending on the oil. Preferably, the oil is nonpolar and highly hydrophobic. In the above, the oil may be determined to be non-admixable with the solution when, under the filtration condition, the oil passes through the membrane filter when not being wetted with the solution whereas the oil does not pass through the membrane filter when being wetted with the solution. If the oil is highly non-admixable with the solution, the oil does not pass through the membrane even after all collectable filtrate of the solution has passed through the membrane. The membrane is wetted with the solution even after completion of filtration, and the remaining solution on the membrane prevents the oil from passing therethrough. However, if the membrane is highly hydrophilic, the oil may not pass through even if no solution is present. In that case, the oil may be determined to be non-admixable with the solution when, under filtration conditions that the oil passes through a membrane filter when not being wetted with the solution, the oil does not pass through the membrane filter when being wetted with the solution.

The oil may be selected from the group consisting of heavy mineral oil, light mineral oil, almond oil, cinnamon oil, and clove oil.

In an embodiment, the membrane filter is disposable. The solution may be a biological solution such as a cell lysate.

Further, in an embodiment, the filtration is conducted by using a pressure difference between a pressure upstream of the membrane filter and a pressure downstream of the membrane filter, preferably without centrifugation. As long as the downstream pressure is lower than the upstream pressure, filtration can be performed. In an embodiment, the downstream pressure may be a suction pressure. The present invention can also be adapted to centrifuge filtration, although formation of bubbles may not occur in centrifuge filtration.

In another aspect of the present invention, a method is provided for preventing formation of bubbles in filtration operation using a membrane. The method comprises placing a layer of an oil on top of a solution-to-be filtered, wherein said oil has a lower specific gravity than the solution and is non-admixable with the solution, wherein the oil does not pass through the membrane under a designated filtration pressure as lone as the membrane is wetted with the solution.

In still another aspect, a method is provided for preventing formation of bubbles in filtration operation using a membrane, comprising placing a layer of an oil on top of a solution-to-be filtered, wherein the oil has a lower specific gravity than the solution and is non-admixable with the solution to the extent that the oil partially penetrates the membrane under a designated filtration pressure when the membrane is wetted with the solution.

In an embodiment, the oil may have a specific gravity in the range of 0.7–1.1 g/m depending on the specific gravity of the solution-to-be filtered. The specific gravity of the oil may be preferably no more than approximately 1.05 g/ml.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

DETAILED DESCRIPTION OF THE PREFERRED EMBODIMENT

Aspects of the present invention provide a method for the prevention of bubble formation and foaming during filtration operation processes. Specifically, according to some embodiments of the present invention, an oil is over-layered on top of a surfactant- or detergent-containing solution prior to the filtration operation process. The selected oil forms a layer on top of the surfactant- or detergent-containing solution. During the filtration operation process, the oil does not pass through the membrane. As the filtration pressure is pulling the solution down through the membrane, the non-admixability and low specific gravity of the selected oil allow the oil to cover the entire surface of the membrane, sealing the solution and filter surface from air. The prevention of air passage through the filter membrane eliminates the formation of bubbles in the filtered solution. Thus, the recovery of the filtered solution is increased. In addition, the filtration pressure can be increased and the filtration time can be extended to further improve the recovery of the solution. Accordingly, the present invention discloses a methodology for obtaining bubble-free solutions during filtration operation processes.

Thus, in a first aspect, the invention relates to a method of preventing formation of bubbles in a filtration operation comprising placing an oil on top of a solution-to-be filtered, wherein the oil is not admixable with the solution and has a lower specific gravity than the solution so that the oil does not pass through the membrane under a designated filtration pressure.

The solution to be used in the methods of the present invention may be any solution comprising a surfactant, a detergent, or other component which would result in the formation of bubbles or foaming during the filtration process.

By surfactants and detergents, it is understood in the art to contain a hydrophilic and hydrophobic component, falling under, but not limited to, ionic, non-ionic, and amphoteric classifications. Ionic detergents are detergent species bearing a net charge, either negative (anionic detergents) or positive (cationic detergents). Examples of anionic detergents include alkyl aryl sulphonates (e.g., dodecylbenzene), long chain (fatty) alcohol sulphates, olefine sulphates and sulphonates, sulphated monoglycerides, sulphated ethers, sulphosuccinates, alkane sulphonates, phosphate esters, alkyl isethionates, and sucrose esters. Some common anionic detergents include sodium dodecyl sulfate (SDS), lithium dodecyl sulfate (LiDS), and lauroylsarcosine. Examples of cationic detergents include the quaternary ammonium salts such as cetyltrimethylammonium bromide (CTAB) and cetyltrimethylammonium chloride (CTAC). Non-ionic detergents have structures in which the hydrophilic region contains many oxygen atoms which can hydrogen bond to water. Common examples of non-ionic detergents include Triton X-100™, Tween™, and Nonidet™.

Oils to be used in the method of the present invention have a lower specific gravity than the solution-to-be filtrated and are non-admixable with the solution so that the solution can thoroughly be covered with the oil and the solution can predominantly pass through the membrane filter, rather than the oil, while the oil prevents formation of bubbles during filtration operation. Oils can be selected based on the conditions of filtration. That is, the pore size of a membrane filter, the required pressure difference, the type of solution-to-be filtrated, the hydrophobicity of the oil against the solution, etc., may be considered. For example, the larger the pore size or the higher the pressure difference, the higher the hydrophobicity of the oil is required. Further, the more the bubble forming substance included, the more the oil is required. Due to various factors involved, an appropriate oil may preferably be selected by advance experiments. The amount of an oil applied on top of a solution-to-be filtered may range from 0.5 to 10.0 $\mu$l/mm$^2$ (preferably 1.25 to 5.0 $\mu$l/mm$^2$, and in an embodiment, approximately 2.5 $\mu$l/mm$^2$), depending on the bubble formation intensity of the solution under filtration conditions. However, the amount of oil does not affect efficiency of filtration and recovery of a filtrate.

The oils usable in the present invention may include mineral oil (e.g. light white oil and heavy white oil), almond oil, clove oil, cinnamon oil, and other oils known in the art. These oils can be used singly or in combination of two or more. Preferred oils are of Molecular Biology grade. Characteristics of the selected oil are that oil is not admixable with the solution to be filtered, and that the specific gravity of the oil is lower than that of the solution to be filtered. Preferably, the non-admixability of the oil is such that the oil does not pass through the filtration membrane during the filtration operation as long as the membrane is wetted with the solution. Alternatively, the oil may be non-admixability such that the oil partially penetrates the filtration membrane. Filtration operation typically includes centrifugation and vacuum filtration.

The specific gravity of the oil will vary depending on the oil selected and the solution to be filtered. In an embodiment, the specific gravity of the oil ranges from about 0.80 g/ml to about 1.05 g/ml, preferably about 0.84 g/ml to about 0.88 g/ml. For example, the specific gravity of light white mineral oil may be approximately 0.84 g/ml. The specific gravity of heavy white mineral oil may be approximately 0.88 g/ml. The specific gravity of almond oil may be approximately 1.05 g/ml. The specific gravity of clove oil may be approximately 1.04 g/ml. The specific gravity of cinnamon oil may be approximately 1.03 g/ml.

Membranes used in the present invention will vary with scope depending on the specific application. Membranes used in the methods of the present invention may include, but are not limited to, glass fiber membranes, polycarbonate membranes (e.g., GenePlate™), hydrophilic polypropylene membranes (e.g., AcroWell™), polytetrafluroethylene membranes (e.g., Emflon®), polyvinylidenedifloride membranes (e.g., BioTrace™ PVDF), nitrocellulose membranes (e.g., BioTrace™ NT), and nylon membranes (e.g., Biodyne®), a multiple well-GF/C glass fiber filter plate (e.g., RiboCap™ filter plate). In an embodiment, membranes of the invention may have a pore size ranging from about 0.2 $\mu$m to about 5.0 $\mu$m. In another embodiment, the pore size may be from about 0.2 $\mu$m to about 1.2 $\mu$m, preferably from about 0.2 $\mu$m to about 0.5 $\mu$m.

The following Examples are not limiting and are used to further describe the present invention:

EXAMPLES

The following Examples were performed using a RiboCap™ filter plate (RNAture, Inc., Calif.) with a glass fiber membrane attached at the bottom, Holder/Wash plate, Perforated Sealing Tape and Lysis buffer, all included in the mRNA Express Kit (RNAture, Inc.) Oils tested in the following Examples were Mineral Oil (Heavy white oil; specific gravity 0.88 g/ml), Mineral Oil (Light white oil, Molecular Biology grade, DNase RNase free, usage for overlaying aqueous reactions; specific gravity 0.84 g/ml), Clove Oil (specific gravity 1.04 g/ml), Cinnamon Oil (specific gravity 1.03 g/ml), and Almond Oil (specific gravity 1.05 g/ml), purchased from Sigma (St. Louis, Mo.). The vacuum manifold utilized was Dynamifold (ACME-Automation, Supplier is RNAture, Inc.) Poly(dimethylsiloxane) fluid of varying viscosity (10,000 cst, 1000 cst, 100 cst, 10 cst, 1 cst, and 0.5 cst) was purchased from Aldrich Chem. (Milwaukee, Wis.).

In each of the following Examples, the Holder/Wash plate was directly placed on Dynamifold, the vacuum manifold and collar were placed over the Holder/Wash plate, and then RiboCap™ filter plate was placed on top of the collar. A pressure gauge was connected to vacuum manifold and vacuum. After the procedures (vacuum filtration or centrifugation) with or without oil were performed, the volume of pass-through fraction was determined.

Example 1

The effect of applying oil over Lysis buffer and the correlation between formation of bubbles and various vacuum pressure at 10, 12, 15 20 30 cmHg was evaluated.

100 $\mu$l of Lysis buffer, which included a surfactant, was applied to 32 wells of a RiboCap™ filter plate and then 50 $\mu$l of Mineral oil was added on top of Lysis buffer in half of the wells (n=16). The unused wells were sealed for proper vacuum using Perforated Sealing Tape. Lysis buffer was vacuumed for 10 seconds. The vacuum pressure was varied by applying 10, 12, 15, 20 and 30 cm of mercury (cmHg). The Holder/Wash plate was examined by eye-observation to determine the presence of bubbles in the tested wells. In addition, the back of the RiboCap™ filter plate was examined to determine if cross-contamination had occurred by the presence of liquid on the nozzle area and neighboring gasket area.

Applying 10 cmHg of vacuum pressure (1.87 psi) for 10 seconds resulted in 6% to 37% of the non-oil covered wells to have foam in the Lysis buffer. No evidence of cross-contamination on the back of the filter plate was observed. As the vacuum pressure was increased, the presence of foam in the non-oil covered wells increased and formation of bubbles was observed in all of the non-oil covered wells when greater than 10 cmHg of vacuum pressure was applied. In addition, at greater than 10 cmHg of vacuum pressure, liquid was observed on the back of the filter plate, and cross-contamination of wells had occurred.

Observation of the 16 oil-covered wells revealed the absence of bubbles in the Lysis buffer at all tested vacuum pressures.

Example 2

Under the same conditions as above, filtration using a new filter was conducted for (a) only the lysis buffer, (b) only the oil, and (c) the lysis buffer covered with the oil. As a result, in (a), the lysis passed through the filter, and in (b), the oil passed through the filter. However, in (c), the oil did not pass through the filter even after the lysis buffer passed through the filter.

Example 3

The effect of varying the vacuum time on Lysis buffer over-layered with oil was evaluated.

Lysis buffer was applied to some wells (n=16) of the RiboCap™ filter plate, and then Mineral oil was over-layered on the Lysis buffer, as in Experiment 1. Vacuum was applied for various times Lysis buffer was vacuumed for various times (10 seconds, 30 seconds, 2 minutes and 5 minutes) at 12 cmHg and recovery volume in each well was measured.

No formation of bubbles was observed in the Lysis buffer at any vacuum time. Results are displayed in Table 1 below. Recovery volumes were increased from 51.6 $\mu$l for 10 seconds to 79.3 $\mu$l for 5 minutes.

TABLE 1

| (n = 16)     | 10 sec | 30 sec | 2 min | 5 min |
|--------------|--------|--------|-------|-------|
| Average ($\mu$l) | 51.6   | 51.8   | 77.6  | 79.3  |
| Stdve        | 3.72   | 6.17   | 5.91  | 7.92  |
| CV           | 7%     | 12%    | 8%    | 10%   |

Example 4

The effect of different oils and different volumes of oil applied over Lysis buffer was evaluated.

Lysis buffer was applied to some wells of the RiboCap™ filter plate and the different oils were added over Lysis buffer as in Experiment 1. Lysis buffer was vacuumed for 30 seconds or 2 minutes at a vacuum pressure of 12 cmHg. The different oils tested and their specific gravity are listed below:

1) Mineral Oil—Heavy white oil (specific gravity: 0.88 g/ml)
2) Mineral Oil—Light white oil, Molecular Biology grade, DNase RNase free usage for overlaying aqueous reactions) (specific gravity: 0.84 g/ml)
3) Clove Oil (specific gravity: 1.04 g/ml)
4) Cinnamon Oil (specific gravity: 1.03 g/ml)
5) Almond Oil (specific gravity: 1.05 g/ml)

No formation of bubbles was observed in the Lysis buffer at a vacuum pressure of 12 cmHg for 30 seconds. Clove oil admixed with the aqueous layer, making the solution turbid. Cinnamon oil went through filter and was located under aqueous layer. Recovery results are shown in Table 2 below. Almond oil and Mineral oil (Light) showed a greater recovery volume at 12 cmHg for 30 seconds.

TABLE 2

| (n = 16)     | Almond | Mineral (Heavy) | Mineral (Light) | Clove* | Cinnamon* |
|--------------|--------|-----------------|-----------------|--------|-----------|
| Average ($\mu$l) | 49.7   | 28.1            | 43.6            | aqueous and oil layer were mixed | Oil layer located under aqueous layer |
| Stdve        | 5.3    | 7.78            | 3.65            |        |           |
| CV           | 11%    | 28%             | 8%              |        |           |

*results not applicable for Average, Stdve and CV.

The vacuum time was increased to 5 minutes. A portion of the Almond oil went through the filter and foam was observed in the Lysis buffer. Recovery results are shown in Table 3 below. Varying the oil volume did not significantly affect the recovery volume, however, a slightly larger recovery was obtained by adding larger volume of oil.

TABLE 3

| (n = 16)     | Almond (100 $\mu$L) | Mineral (Heavy) (100 $\mu$L) | Mineral (Light) (100 $\mu$L) | Mineral (Heavy) (50 $\mu$L) |
|--------------|---------------------|------------------------------|------------------------------|-----------------------------|
| Average ($\mu$l) | 71.25               | 47.1                         | 86.7                         | 82.6                        |
| Stdve        | 13.14               | 2.05                         | 5.13                         | 4.05                        |
| CV           | 18%                 | 4%                           | 6%                           | 5%                          |

Example 5

The efficiency and reproducibility of the centrifugation and vacuum manifold method was compared.

Lysis buffer was applied to some wells of two RiboCap™ filter plates, and then Mineral oil was over-layered on top of the Lysis buffer. One of the RiboCap™ filter plates was vacuumed for 2 minutes at 12 cmHg with Dynamifold, vacuum manifold. The other RiboCap filter plate was placed over Holder/Wash plate, and underwent centrifugation at 3000×g for 5 minutes. In addition, Lysis buffer without mineral oil was vacuumed for 30 seconds at 12 cmHg in 16 wells.

Formation of bubbles was present in the 16 wells without oil vacuumed for 30 seconds. Recovery results are in Table 4 below. The vacuum manifold method (12 cmHg, 2 minutes) with oil over Lysis buffer was able to obtain similar recovery and CV as centrifugation (3000×g, 5 minutes) of the Lysis buffer. By applying oil over the Lysis buffer and vacuuming for 2 minutes, the recovery volume increased from 67.4 µl (30 seconds, no oil) to 86.7 µl (with oil) without creating foam. In the case of not adding oil, excessive vacuum time (longer than 30 seconds), foaming of the Lysis buffer occurred.

TABLE 4

| (n = 16) | Centrifugation 3000× g, 5 min | 12 cmHg, 2 min Mineral (Light) 100 µl | 12 cmHg, 30 sec. without Oil |
|---|---|---|---|
| Average (µl) | 86.75** | 86.69 | 67.4 |
| Stdve | 1.13 | 5.13 | 3.03 |
| CV | 1.3% | 5.9% | 4.0% |

**RiboCap ™ filter plate has some dead volume, so that 86.8% recovery can be considered as 100%.

The Examples described above are set forth solely to assist in the understanding of the invention. It is to be understood that variations of the invention, including all equivalents now known or later developed, are to be considered as falling within the scope of the invention, which is limited only by the following claims.

What is claimed is:

1. A method of filtration comprising:
   loading a solution-to-be filtrated upstream of a membrane filter, said solution containing components forming bubbles during filtration operation;
   covering the solution with a layer of an oil composition, said composition consisting essentially of at least one oil, to prevent formation of bubbles from the solution, said at least one oil being non-admixable with the solution and having a lower specific gravity than the solution;
   filtrating the solution through the membrane filter wherein the oil stays on the membrane filter; and
   recovering a filtrate.

2. The method according to claim 1, wherein the oil is non-admixable with the solution when, under the filtration condition, the oil passes through the membrane filter when said filter is not wetted with the solution whereas the oil does not pass through the membrane filter when said filter is wetted with the solution.

3. The method according to claim 1, wherein the filtration is conducted by using a pressure difference between a pressure upstream of the membrane filter and a pressure downstream of the membrane filter.

4. The method according to claim 3, wherein the downstream pressure is a suction pressure.

5. The method according to claim 1, wherein the oil is selected from the group consisting of heavy mineral oil, light mineral oil, almond oil, cinnamon oil, and clove oil.

6. The method according to claim 1, wherein the membrane filter is disposable.

7. The method according to claim 1, wherein the solution is a biological solution containing a surfactant or detergent.

8. The method according to claim 7, wherein the solution is a cell lysate.

9. A method of preventing formation of bubbles in filtration operation using a membrane, comprising placing a layer of an oil composition, said composition consisting essentially of at least one oil, on top of a solution-to-be filtered, said at least one oil having a lower specific gravity than the solution and being non-admixable with the solution, wherein the oil does not pass through the membrane under a designated filtration pressure as long as the membrane is wetted with the solution.

10. The method of claim 9, wherein said oil is selected from the group consisting of heavy mineral oil, light mineral oil, almond oil, cinnamon oil and clove oil.

11. The method of claim 9, wherein said oil has a specific gravity of no more than approximately 1.05 g/ml.

12. A method of filtering a solution with reduced bubble formation relative to filtering the solution alone, comprising placing a layer of an oil composition that consists essentially of at least one oil on top of a solution-to-be filtered, said at least one oil having a lower specific gravity than the solution and being non-admixable with the solution; filtering the solution through a membrane for at least 30 seconds under a designated filtration pressure, wherein the oil composition does not completely penetrate the membrane.

13. The method of claim 12, wherein said oil is selected from the group consisting of heavy mineral oil, light mineral oil, and almond oil.

14. The method of claim 13, wherein said oil has a specific gravity of no more than approximately 1.05 g/ml.

15. The method of claim 9, wherein said oil has a specific gravity of between about 0.7 and about 1.1 g/ml.

16. The method of claim 11, wherein said oil has a specific gravity of between about 0.84 and about 0.88 g/ml.

17. The method of claim 13, wherein said oil has a specific gravity of between about 0.7 and about 1.1 g/ml.

18. The method of claim 14, wherein said oil has a specific gravity of between about 0.84 and about 0.88 g/ml.

* * * * *